United States Patent
Zabara

(10) Patent No.: US 7,422,555 B2
(45) Date of Patent: Sep. 9, 2008

(54) SYSTEMS AND METHODS FOR THERAPEUTICALLY TREATING NEURO-PSYCHIATRIC DISORDERS AND OTHER ILLNESSES

(76) Inventor: Jacob Zabara, 300 S. Pointe Dr., Apt. 2002, Miami Beach, FL (US) 33139

( * ) Notice: Subject to any disclaimer, the term of this patent is extended or adjusted under 35 U.S.C. 154(b) by 825 days.

(21) Appl. No.: 10/780,806

(22) Filed: Feb. 18, 2004

(65) Prior Publication Data

US 2005/0182288 A1 Aug. 18, 2005
US 2006/0052657 A9 Mar. 9, 2006

Related U.S. Application Data

(60) Provisional application No. 60/533,656, filed on Dec. 30, 2003.

(51) Int. Cl.
A61B 17/52 (2006.01)
A61N 1/00 (2006.01)

(52) U.S. Cl. .............................. 600/9; 607/3
(58) Field of Classification Search ......... 128/897–889; 600/9–15, 373, 378, 544, 545; 607/1–3, 607/30–33, 44–46, 48, 50, 58–60, 65–66, 607/103, 115–116, 118, 139
See application file for complete search history.

(56) References Cited

U.S. PATENT DOCUMENTS

| 4,765,310 | A | | 8/1988 | Deagle et al. |
| 4,940,453 | A | * | 7/1990 | Cadwell ....................... 600/13 |
| 5,299,569 | A | | 4/1994 | Wernicke et al. |
| 5,540,734 | A | | 7/1996 | Zabara |
| 6,132,361 | A | | 10/2000 | Epstein et al. |
| 6,266,556 | B1 | | 7/2001 | Ives et al. |
| 6,356,788 | B2 | * | 3/2002 | Boveja ......................... 607/45 |
| 6,425,852 | B1 | * | 7/2002 | Epstein et al. ................ 600/13 |
| 2003/0050527 | A1 | * | 3/2003 | Fox et al. ...................... 600/13 |
| 2003/0074032 | A1 | * | 4/2003 | Gliner .......................... 607/45 |
| 2004/0049240 | A1 | | 3/2004 | Gerber et al. |
| 2005/0033379 | A1 | | 2/2005 | Lozano et al. |

* cited by examiner

Primary Examiner—Samuel G Gilbert
(74) Attorney, Agent, or Firm—David J. Muzilla; Hahn Loeser & Parks, LLP

(57) ABSTRACT

Systems and methods for treating neuro-psychiatric disorders, such as depression or schizophrenia, and/or other illnesses are disclosed. A patient is diagnosed with a particular neuro-psychiatric disorder or other illness. An electric nerve stimulation (ENS) technique, such as vagus nerve stimulation (VNS), is administered to the patient in conjunction with a magnetic nerve stimulation (MNS) technique. The magnetic nerve stimulation (MNS) technique includes applying a magnetic field to a pre-selected synaptic region of a brain of the patient based on the diagnosis. A physiological response of the brain, such as electroencephalogram (EEG) activity, is monitored. One or more parameters of the magnetic field may be selectively adapted in response to the monitored physiological response. The administration of the ENS technique and the MNS technique may be performed simultaneously, in serial order, or in alternating order depending on the diagnosis.

26 Claims, 7 Drawing Sheets magnetic stimulation (MS) subsystem

SYSTEMS AND METHODS FOR THERAPEUTICALLY TREATING NEURO-PSYCHIATRIC DISORDERS AND OTHER ILLNESSES

CROSS-REFERENCE TO RELATED APPLICATIONS/INCORPORATION BY REFERENCE

This application claims priority to U.S. provisional patent application Ser. No. 60/533,656 filed on Dec. 30, 2003, Express Mail number EV415640672US.

U.S. Pat. No. 5,299,569 issued on Apr. 5, 1994 is incorporated by reference herein in its entirety. U.S. Pat. No. 5,540,734 issued on Jul. 30, 1996 is incorporated by reference herein in its entirety. U.S. Pat. No. 6,132,361 issued on Oct. 17, 2000 is incorporated by reference herein in its entirety. U.S. Pat. No. 6,266,556 issued on Jul. 24, 2001 is incorporated by reference herein in its entirety.

TECHNICAL FIELD

The present invention relates to systems and methods for treating or controlling medical, psychiatric, or neurological disorders and conditions. More particularly, certain embodiments of the present invention relate to using an electric nerve stimulation (ENS) technique in conjunction with a magnetic stimulation (MS) technique to treat the disorders. The ENS technique may comprise vagus nerve stimulation (VNS) and the MS technique may comprise a magnetic nerve stimulation (MNS) technique for stimulation of the vagus nerve or other cranial nerves.

BACKGROUND OF THE INVENTION

Most nerves in the human body are actually nerve bundles composed of thousands of individual neurons (nerve fibers). These nerve fibers have different sizes designated as A, B, and C fibers, and they carry signals to and from the brain and other parts of the body. The vagus nerve, for example, may have approximately 100,000 fibers of the three different types, each of which carries such signals. Each fiber of that nerve bundle only conducts in one direction in normal circumstances. The A and B fibers are myelinated, that is, they have a myelin sheath in the form of a substance largely composed of fat. The C fibers, however, are unmyelinated.

Myelinated fibers are typically larger, have faster electrical conduction and much lower electrical stimulation thresholds than unmyelinated fibers. Myelinated fibers also exhibit a particular strength-duration curve in response to a specific width and amplitude of stimulation pulse.

The A and B fibers are stimulated by electrical pulses having relatively narrow pulse widths, from 50 to 200 microseconds, for example. The A fibers exhibit slightly faster electrical conductivities than the B fibers, and have slightly lower electrical stimulation thresholds. Compared to A and B fibers, C fibers are relatively much smaller, conduct electrical signals very slowly, and have high stimulation thresholds typically requiring wider pulse widths (e.g., 300-1000 microseconds) and higher amplitudes for activation. Although the A and B fibers may be selectively stimulated without also stimulating the C fibers, the magnitude and width of the pulse required for stimulating the C fibers would also activate A and B fibers.

As noted above, individual fibers of the vagus nerve normally conduct electrical signals in only one direction. Electrical stimulation of the vagus nerve bundle typically activates sufficient fibers to generate neural signals in both directions (bi-directionality). However, selective unidirectional stimulation is achievable through the use of special nerve electrodes and stimulating waveforms.

A neurostimulator device may be used to selectively and electrically modulate a nerve, such as the vagus nerve. The neurostimulator may be entirely implantable, used primarily external to the body with only a small portion of the circuitry implanted, used almost entirely external to the body with only the nerve electrode(s) and associated lead(s) implanted percutaneously. Whether fully or partially implanted, the disorders treatable, controllable or preventable by such nerve stimulation devices include voluntary and involuntary disorders, migraine, epileptic seizure, motor disorders, Parkinson's disease, cerebral palsy, spasticity, chronic nervous illnesses and involuntary movement; pancreatic endocrine disorders including diabetes and hypoglycemia; dementia including cortical, subcortical, multi-infarct, Alzheimer's disease and Pick's disease; sleep disorders including central sleep apnea, insomnia and hypersomnia; eating disorders including anorexia nervosa, bulimia and compulsive overeating; and neuropsychiatric disorders including schizophrenia, depression and borderline personality disorder. One particularly common ENS technique is known as vagus nerve stimulation (VNS), because the stimulation is directed specifically to the vagus nerve. The effect of VNS is to change the polarization of synaptic membranes in nuclei or centers of the brain, resulting in a reduction or cessation of the neuropsychiatric disorder being treated.

VNS was approved by the Food and Drug Administation (FDA) for therapy in refractory epilepsy in 1997. Although effective for many patients, improvements in the technology are desirable. More particularly, only a portion of refractory epileptic patients cease seizures almost immediately, whereas most patients show a gradual decline in seizure rates for a period of months to years after initiating VNS therapy. In addition, the therapy is either ineffective or only marginally effective for some patients. Also, other illnesses, such as cancer, are not significantly affected by VNS therapy alone.

Magnetic stimulation (MS) techniques are also used to diagnose a number of medical conditions, including specifically neurological and psychiatric disorders. Magnetic stimulation (MS) refers generally to magnetic nerve stimulation (MNS) therapy that is applied specifically to nerve tissue. One particularly well-known clinical diagnostic technique is transcranial magnetic stimulation (TMS). TMS is a technique for stimulating the human brain non-invasively by using the principle of inductance to transmit electrical energy across the scalp and skull of the patient without the pain associated with direct percutaneous electrical stimulation. It involves placing a coil of wire on the scalp and passing a powerful and rapidly changing current through it. This produces a magnetic field which passes unimpeded and relatively painlessly through the tissues of the head. The magnetic field, in turn, induces a weak electrical current in the brain. The strength of the induced current is a function of the rate of change of the magnetic field, which is determined by the rate of change of the current in the coil. In order to induce enough current to depolarize neurons in the brain, the current passed through the stimulating coil must start and stop or reverse its direction within a few hundred microseconds. Additional details on TMS are provided in U.S. Pat. Nos. 6,132,361 and 6,266,556, both hereby incorporated by reference.

Further limitations and disadvantages of conventional, traditional, and proposed approaches will become apparent to persons of skill in the art, through comparison of such systems with the present invention as set forth in the remainder of the present application with reference to the drawings.

BRIEF SUMMARY OF THE INVENTION

An embodiment of the present invention provides a method for treating neuro-psychiatric disorders and/or other illnesses. The method comprises diagnosing a neuro-psychiatric disorder and/or other illness of a patient. The method further comprises administering an ENS technique, such as VNS, to the brain of the patient in conjunction with an MS technique, preferably an MNS technique such as TMS.

An embodiment of the present invention provides a system for the therapeutic treatment of neuro-psychiatric disorders or other illnesses of a patient. The system comprises a magnetic stimulation (MS) subsystem to generate a pulsed current waveform to produce a pulsed magnetic field which stimulates a first location within the body of a patient. The MS subsystem preferably comprises an MNS subsystem to stimulate the brain and/or one or more nerves of the patient. The system also includes an electric nerve stimulation (ENS) subsystem, such as a VNS system, to generate electric signals to stimulate a second location within the body of the patient. The second location preferably comprises at least one nerve of the patient. More preferably, the ENS subsystem stimulates a nerve, such as the vagus nerve, that maps into the brain of the patient. A computer-based switching subsystem is connected to the MS subsystem and the ENS subsystem to select the MS subsystem and/or the ENS subsystem to stimulate the nerves of the patient.

These and other advantages and novel features of the present invention, as well as details of an illustrated embodiment thereof, will be more fully understood from the following description and drawings.

DETAILED DESCRIPTION OF THE INVENTION

In accordance with an embodiment of the present invention, MS allows for an augmentation of present ENS therapies such as VNS by providing MS therapy to a patient before, during, or after the patient is treated with ENS therapy In a preferred embodiment, both MS and ENS therapies are provided to the patient repeatedly. MS allows a range of tissues, such as cranial nerves, to have signal traffic modified by an external magnetic generator. Without being bound by theory, it is believed that using MS therapy in conjunction with ENS therapy improves safety and increases the potential effectiveness of ENS. MS also allows an extension of ENS to treatment of other illnesses such as, for example, cancer and HIV infections by providing a combined action on brain regulatory areas and pathological tissue. MS increases the physiological magnitude of the action to increase possible effectiveness of VNS or the electrical stimulation of other cranial nerves.

Figure 1:
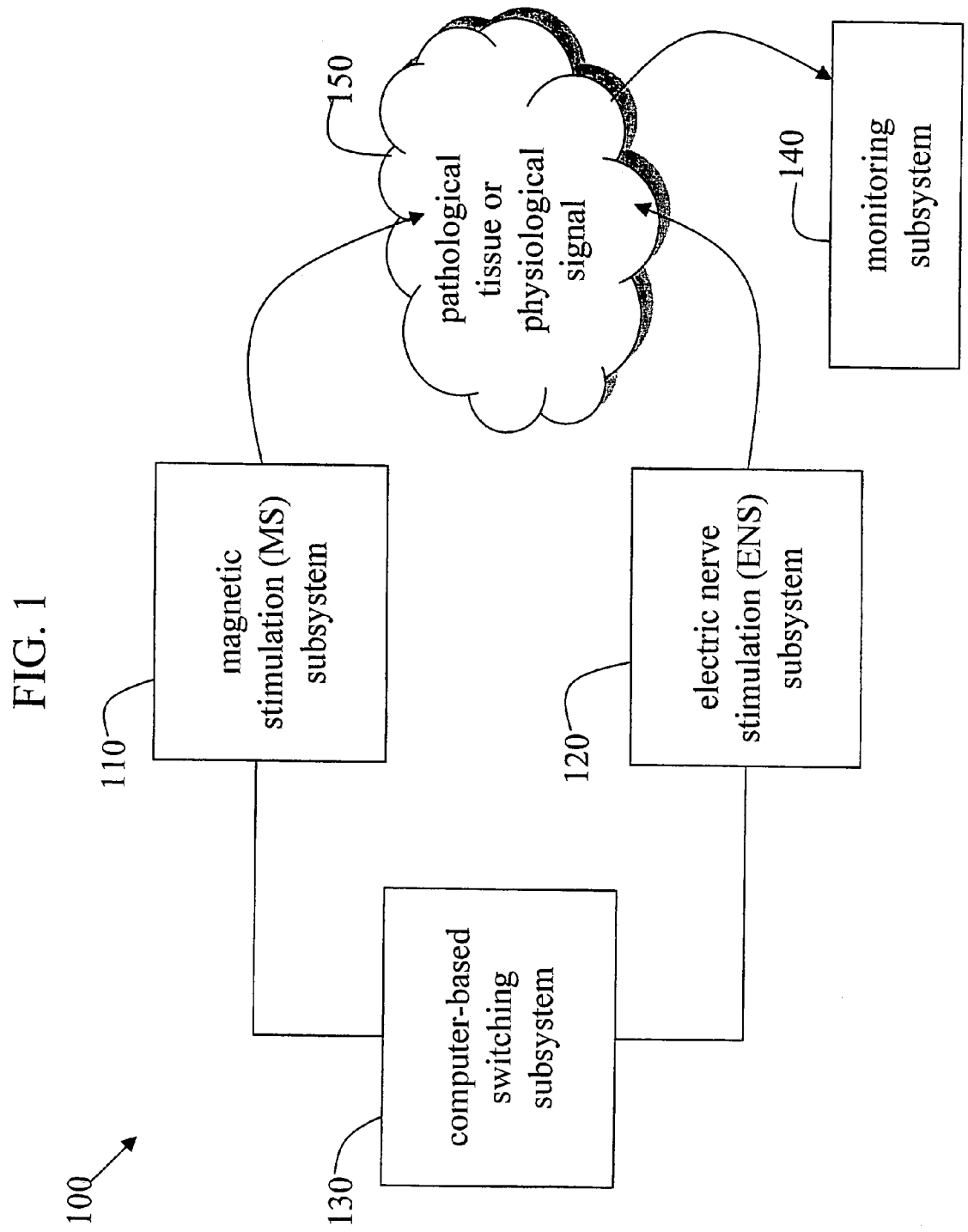
FIG. 1 is a schematic block diagram of an embodiment of a system providing the therapeutic treatment of neuro-psychiatric disorders and other illnesses, in accordance with various aspects of the present invention.

FIG. 1 is a schematic block diagram of an embodiment of a system 100 providing the therapeutic treatment of neuro-psychiatric disorders and other illnesses, in accordance with various aspects of the present invention. The system 100 includes a magnetic stimulation (MS) subsystem 110, an electric nerve stimulation (ENS) subsystem 120, a computer-based switching subsystem 130 connected to the MS subsystem 110 and the ENS subsystem 120, and a monitoring subsystem 140. In accordance with an embodiment of the present invention, the ENS subsystem 120 comprises a VNS system, and the MS subsystem comprises a TMS system. In an alternative embodiment (not shown), the MS subsystem 110 and the ENS subsystem 120 may be provided without coupling the two subsystems to a switching subsystem 130. In a still further embodiment, the MS subsystem 100 and the ENS subsystem 120 may each be provided with separate computer-based switching subsystems.

In accordance with an embodiment of the present invention, the ENS subsystem connects to pathological tissue 150 via, for example, implanted electrodes. Monitoring subsystem 140 connects to the patient via electrodes mounted on the skin of the patient, typically on the scalp, although other monitoring connection sites are possible. In accordance with an embodiment of the present invention, the monitoring subsystem 140 comprises an electroencephalogram (EEG) system. The MS subsystem 110 interacts with the pathological tissue 150 by altering physiological signals within the tissue 150 without the need for direct contact with the tissue. The tissue 150 treated by the MS subsystem 110 may include cranial nerves, specific areas of the brain, or tissues remote from the brain, such as a tumor site in an organ or bone.

Multiple sites of action for the system 100 are possible. For example, multiple nerves may be stimulated at multiple sites by ENS and/or MS, or specific sites (e.g., nuclei) of the brain may be acted upon by MS in addition to ENS. The ENS technique may be administered to a first set of nerves in a brain and the MS technique may be administered to a second set of nerves in the brain. Alternatively, both ENS and MS may be administered to a same set of nerves within the brain. In yet another embodiment, the ENS subsystem may be used to stimulate one or more nerves such as the vagus nerve, and the MS subsystem may be used to stimulate tissue remote from the brain such as organ or bone tissue.

Complex disease states involving different pathological entities can be treated simultaneously. For example, a cancer patient may exhibit symptoms of depression and pain which can be treated by MS in conjunction with VNS. Certain major illnesses, not effectively treatable by VNS alone, may be treated by combined MS and ENS therapy, including cancer and H.I.V.

The computer-based switching subsystem 130 allows for temporally controlling the application of ENS and MS to the patient. The time difference between the application of ENS and the application of MS can be automatically adjusted by the computer-based switching subsystem 130 or manually by an operator via the subsystem 130 to achieve maximum therapeutic effectiveness.

Figure 2:
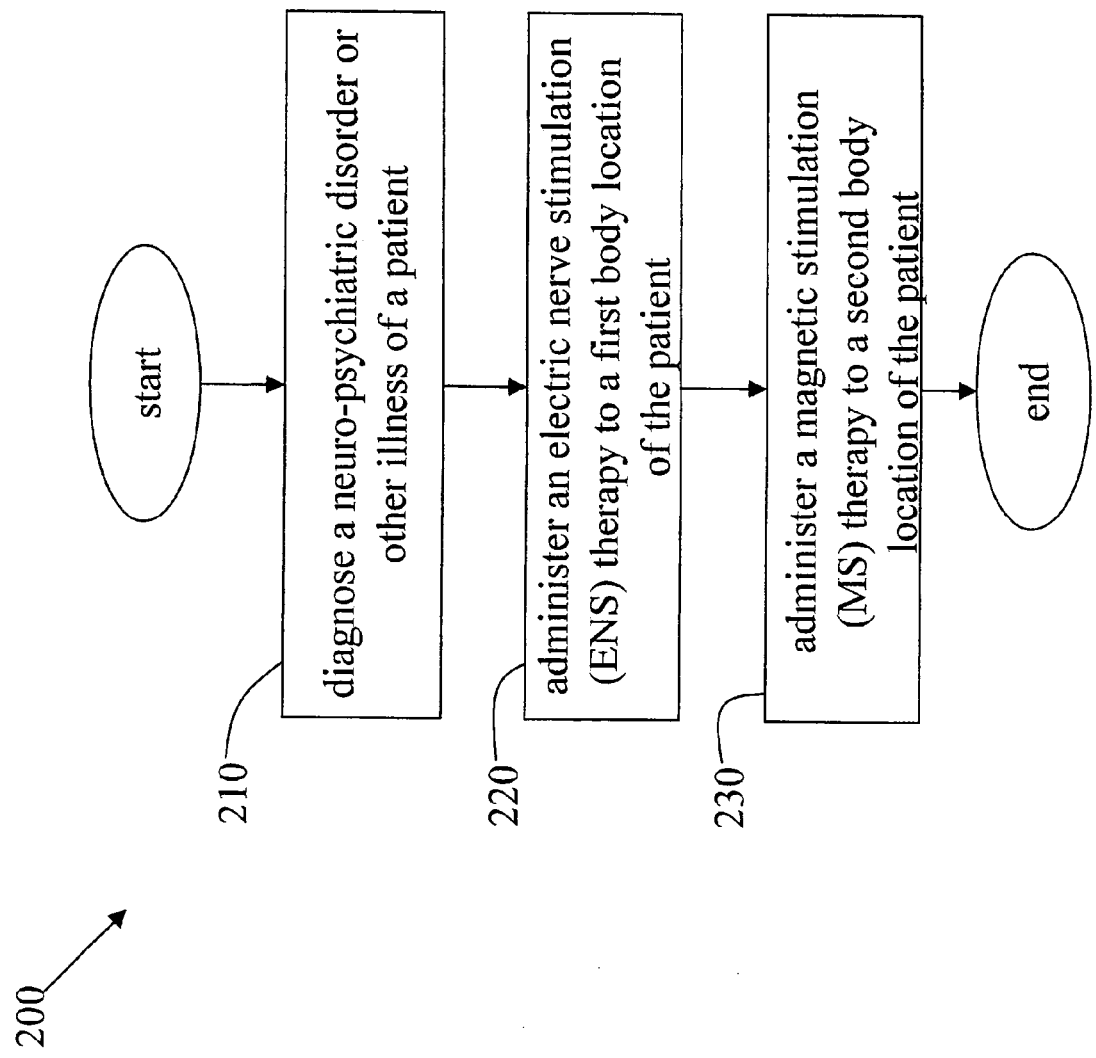
FIG. 2 is a flowchart of a method for treating neuro-psychiatric disorders and other illnesses, using the system of FIG. 1, in accordance with an embodiment of the present invention.

FIG. 2 is a flowchart of a method 200 for treating neuro-psychiatric disorders and other illnesses, using the system 100 of FIG. 1, in accordance with an embodiment of the present invention. In step 210, a patient is diagnosed with a neuro-psychiatric disorder or other illness. In step 220, an electric nerve stimulation (ENS) technique is administered to a first body location of the patient. In a preferred embodiment, the first body location is the brain of the patient. The ENS may be delivered to the brain indirectly by stimulation of a nerve such as the vagus nerve that maps into an area of the brain. In step 230, a magnetic stimulation (MS) technique is administered to a second body location of the patient, which may comprise the brain, one or more nerves, or body locations remote from the brain. In a preferred embodiment, the ENS technique comprises VNS and the MS technique is administered to a brain area of the patient.

In accordance with various embodiments of the present invention, ENS and MS may be administered to the first and second body locations of the patient at the same time, one before the other, or in an alternating manner. Both ENS and MS are preferably delivered repeatedly to the patient. Such specifics of administration depend on the disorder or illness as well as other particulars about the patient.

ENS may be administered as vagus nerve stimluation (VNS) as described in U.S. Pat. No. 5,299,569 issued on Apr. 5, 1994 which is incorporated by reference herein in its entirety, in accordance with an embodiment of the present invention. MS may be administered to the patient as TMS following known parameters.

Without being bound by theory, it is believed that one effect of VNS is to change the polarization of synaptic membranes in nuclei or centers of the brain. In one embodiment of the present invention MS augments the effect of VNS by inducing a current within the brain that directly changes the polarization level. Polarization and depolarization are the methods of electrical charging and discharging within the brain which propagate an impulse along a nerve fiber. A neuron at rest is considered polarized due to its non-zero potential. Hyper-polarization refers to a positive polarization change or an increase in non-zero potential of a neuron (i.e., the neuron is more polarized and is less likely to fire). Depolarization refers to a negative polarization change or a decrease in the non-zero potential of a neuron (i.e., the potential of the neuron comes closer to zero and the neuron is more likely to fire).

A positively directed induced current produces a positive polarization change (hyper-polarization) and a negatively directed induced current produces a negative polarization change (depolarization). Hyper-polarization causes a decrease in EEG frequency (synchronization) within certain synaptic regions of the brain. Depolarization causes an increase in EEG frequency (de-synchronization) within certain synaptic regions of the brain. The types of currents that are induced in the brain of a patient by MS include bi-phasic damped induced currents and poly-phasic damped induced currents.

Systems and methods of the present invention offer the advantage of treating a wide variety of conditions with a minimal surgical profile. In particular, MS need not involve surgical intervention at all, while ENS therapy such as VNS involves only minor surgery with little trauma to the patient. In addition, MS can be used to activate nerves which are difficult to reach by ENS, thus offering the possibility of extending the range of conditions treatable with conventional ENS therapies, such as VNS.

In the brain, MS acts on nuclear synaptic areas including cell bodies, dendrites, and pre-synaptic terminals where there is membrane potential but no action potential. The redistribution of ions within the synaptic areas causes local changes in membrane potential. Synaptic membranes are modeled as a resistor and a capacitor in parallel. The product of the resistor value and capacitor value determines the time constant of a synaptic membrane. A change in membrane voltage is proportional to the applied charges if the rise time is short enough and the duration of stimulus is equal to or less than the time constant of the nuclear membrane. Each nuclear mass (i.e., membrane) has its own average time constant to which electrical and magnetic adjustments of MNS can address. Polarization of synaptic areas is a function of an amount of charge applied, duration of the stimulus, peak value of the stimulus, and time constant of the membrane. If the polarization level of a neuron exceeds a firing threshold, the neuron will fire and propagate a signal.

In accordance with an embodiment of the present invention, induced currents are concentrated in the gray areas of the brain containing the synaptic systems. The white areas of the brain, which contain axons, have low density currents due to the high resistivity of the axon sheaths. As a result, the synaptic areas are more sensitive to induced currents than the axonal regions and, therefore, lower currents can be used during therapy than are necessary to stimulate axonal action potentials (nerve firings).

In one embodiment ENS and MS are implemented so as to reach their maximum polarization result simultaneously or nearly so. VNS usually takes longer to achieve its maximum polarization result than an MS therapy such as TMS. Accordingly, ENS may be administered before administering MS to take into account nerve conduction time, etc. MS has the advantage that it can act almost instantaneously upon the synaptic systems to be polarized.

However, there are instances where it is desirable to administer ENS and MS with different temporal projections. One result of this would be to lengthen or shorten the polarization effect. Also, it may be desirable to create a "frequency" effect by administering ENS and MS in a rapidly alternating series of electrical and magnetic pulses. In accordance with various embodiments of the present invention, there are many possible combination patterns for administering ENS and MS which depend on the specific disease and the condition of the patient.

When MS is administered, it is possible to produce a current within the brain that generates a motor seizure (a sudden, excessive discharge of nerve electrical activity that affects motor control) in the patient. Motor seizures can be prevented by limiting the application of MS to non-motor areas of the brain (e.g., making sure the magnetic field avoids the motor cortex area of the brain). By keeping the magnetic field away from motor areas of the brain, the MS technique will not generate currents within the brain that cause motor seizures.

Also, when MS is administered, it is possible to produce a current within the brain that generates an EEG seizure without producing a motor seizure. An EEG seizure is a sudden, excessive discharge of nerve electrical activity that is only detectable via monitoring of EEG activity.

Figure 3:
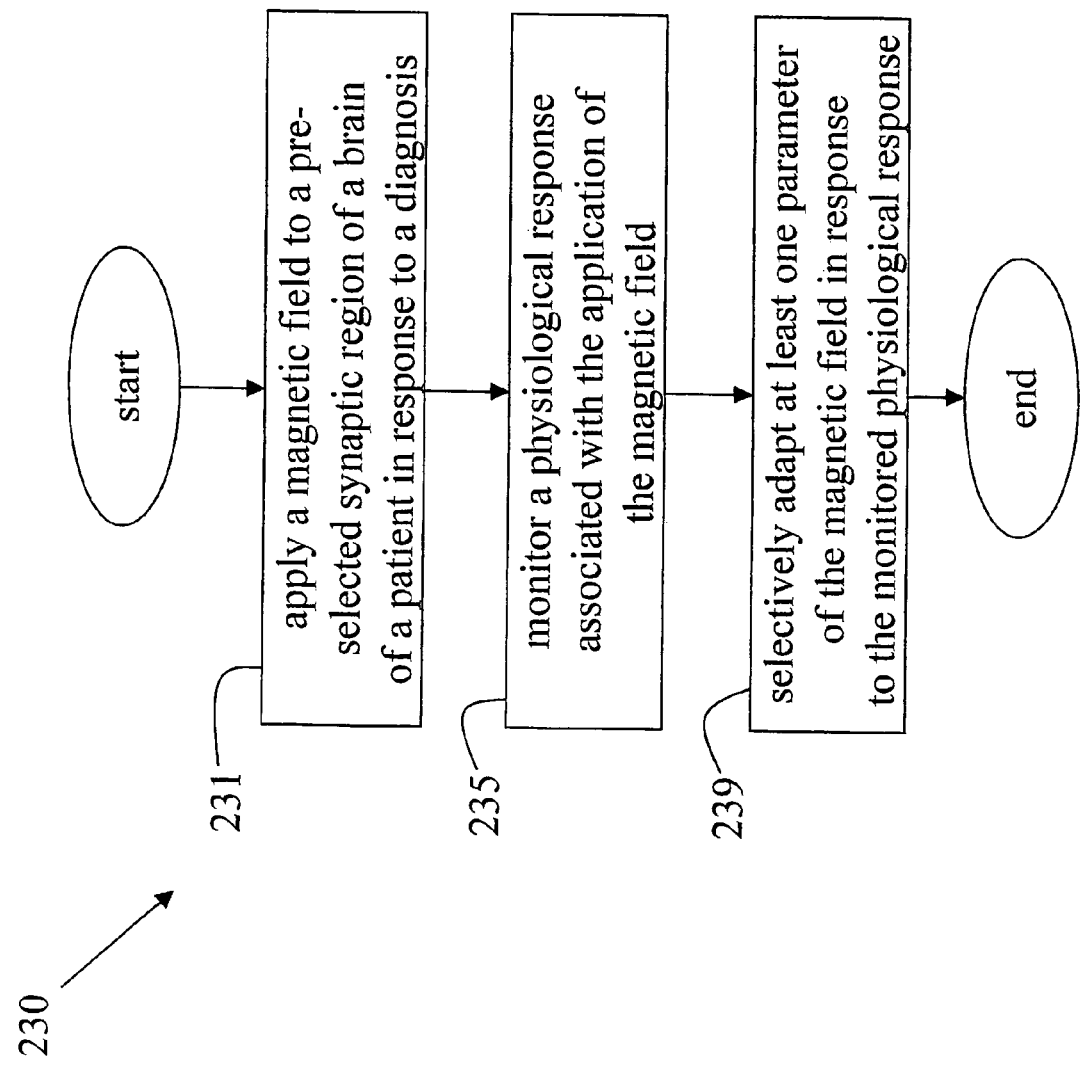
FIG. 3 is a more detailed flowchart of part of the method of FIG. 2 for administering a magnetic stimulation technique to the brain of a patient, using the system of FIG. 1, in accordance with an embodiment of the present invention.

FIG. 3 is a more detailed flowchart of a particular embodiment of step 230 of the method 200 of FIG. 2 for administering a magnetic stimulation technique to a second body location of a patient, using the system 100 of FIG. 1. In step 231, a magnetic field is applied to a pre-selected synaptic region of the brain of the patient in response to the diagnosis. In step 235, a physiological response associated with the application of the magnetic field is monitored. In step 239, at least one parameter of the magnetic field is selectively adapted in response to the monitored physiological response.

In accordance with an embodiment of the present invention, the monitored physiological response comprises electroencephalogram (EEG) activity of the brain of the patient. Other physiological monitoring methods, such as neuroimaging, may alternatively be used. The magnetic field may comprise a pulsed magnetic field, an alternating magnetic field, or a steady magnetic field, in accordance with various aspects of the present invention. Parameters of the MS subsystem 110 may be tailored to specific disease states and conditions or to specific locations within the body of the patient. The parameters that may be selectively adapted include a pulse shape of the magnetic field, a magnetic field strength of the magnetic field, a pulse width of the magnetic field, a pulse repetition frequency of the magnetic field, an alternating frequency of the magnetic field, and an orientation of the magnetic field. In accordance with an embodiment of the present invention, a pulse repetition frequency of the magnetic field ranges between 0.1 Hz and 5000 Hz, more preferably 0.5 Hz and 1000 Hz, even more preferably 0.5 to 500 Hz. An optimum pulse repetition rate is selected for each synaptic system as determined by the time constant of the synaptic equivalent capacitance.

For example, an operator may observe, upon application of an initial MS waveform, that the EEG activity of the patient is exhibiting a first modulation response which is not the desirable response. The operator may then increase the magnetic field intensity of the MS waveform by a certain amount and observe that the EEG activity has changed to yield the desired modulation response which indicates that the MS waveform is having the desired therapeutic effect (e.g., is reducing the symptoms).

Figure 4:
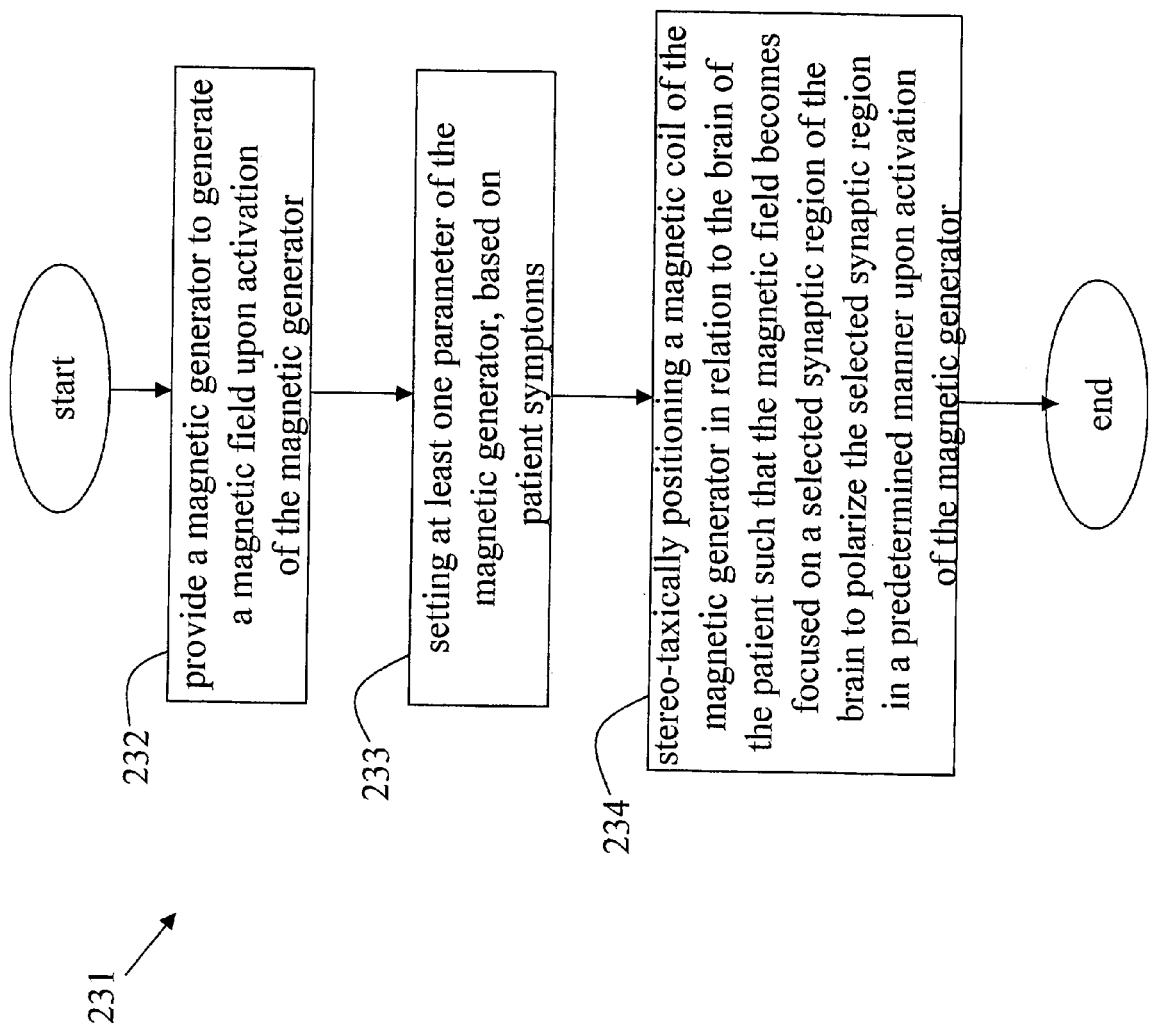
FIG. 4 is a more detailed flowchart of part of the method of FIG. 3 for applying a magnetic field to a pre-selected synaptic region of the brain of the patient, using the system of FIG. 1, in accordance with an embodiment of the present invention.

FIG. 4 is a more detailed flowchart of a particular embodiment of step 231 of the method 230 of FIG. 3 for applying a magnetic field to a pre-selected synaptic region of the brain of the patient, using the system of FIG. 1, in accordance with an embodiment of the present invention. In step 232, a magnetic generator is provided to generate a magnetic field upon activation of the magnetic generator. In step 233, at least one parameter of the magnetic generator is set based on the symptoms of the patient. In step 234, a magnetic coil of the magnetic generator is stereo-taxically positioned in relation to the brain of the patient such that the magnetic field becomes focused on a selected synaptic region of the brain to polarize the selected synaptic region in a predetermined manner upon activation of the magnetic generator. Stereo-taxic positioning is a technique that uses a three-dimensional coordinate system to locate specific areas of the brain.

Figure 5:
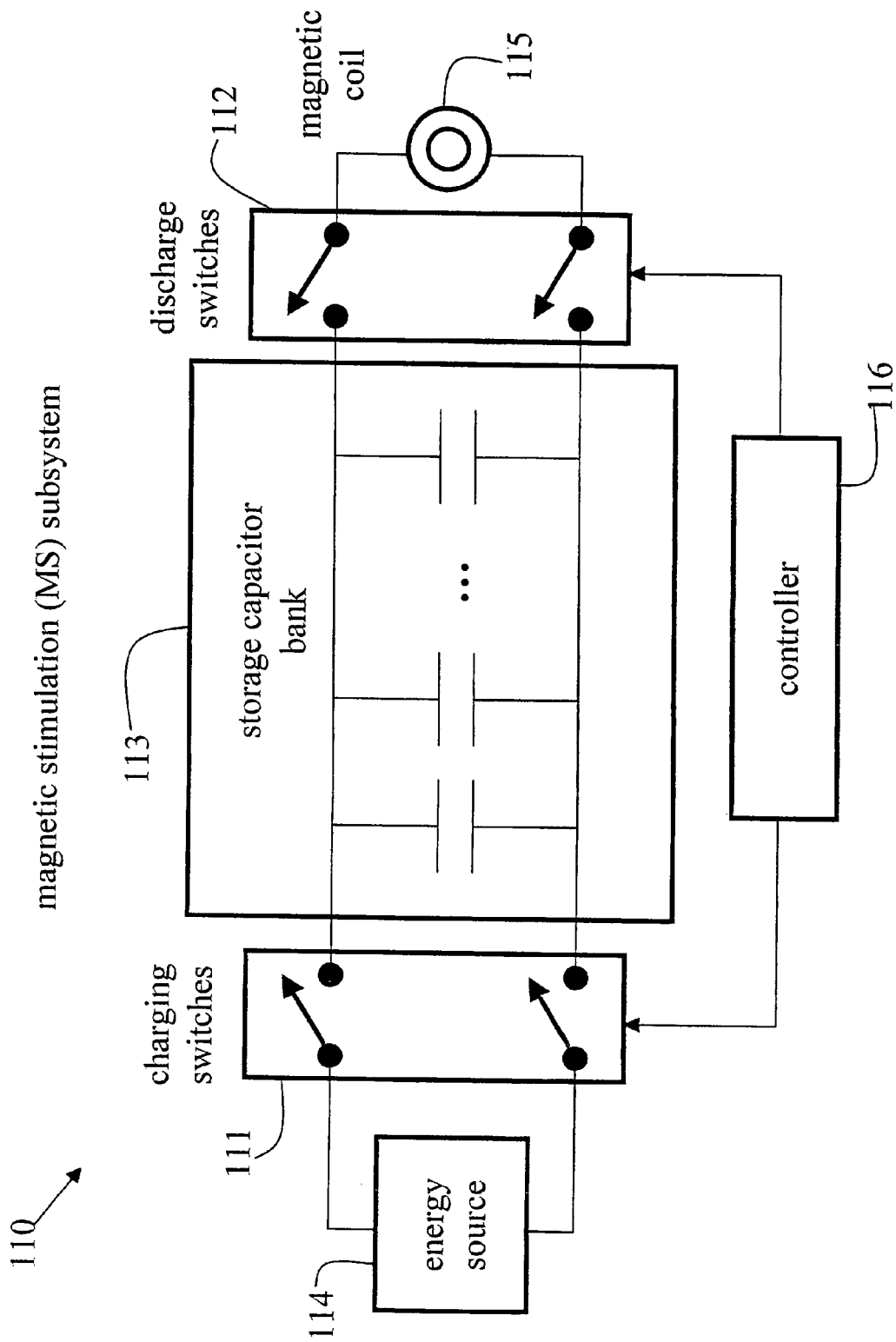
FIG. 5 is a schematic block diagram of an embodiment of a magnetic stimulation (MS) subsystem used in the system of FIG. 1, in accordance with various aspects of the present invention.

FIG. 5 is a schematic block diagram of an embodiment of a magnetic stimulation (MS) subsystem 110 used in the system 100 of FIG. 1, in accordance with various aspects of the present invention. The MS subsystem 110 comprises a configuration of charging switches 111, discharge switches 112, and a storage capacitor bank 113. The MS subsystem 110 further comprises an energy source 114, a magnetic coil 115, and a controller 116. The energy source 114 electrically connects to the charging switches 111 via an input to the configuration of switches and storage capacitors. The charging switches 111 electrically connect to an input of the storage capacitor bank 113. The output of the storage capacitor bank 113 electrically connects to the discharge switches 112. The discharge switches 112 electrically connect to the magnetic coil 115 via an output of the configuration of switches and storage capacitors. The controller 116 electronically connects to the charging switches 111 and the discharge switches 112 to control the operation of the MS subsystem 110.

In accordance with an embodiment of the present invention, the magnetic coil 115 may comprise a plurality of coils arranged in different spatial planes to generate a magnetic field that is focused in a specific manner, such as to precise locations in deep synaptic structures within the brain. Also, the magnetic coil 115 is preferably connected to the configuration of switches and storage capacitors via a flexible, high power cable. The flexible cable allows for easy positioning of the magnetic coil 115. For example, a central axis of a magnetic coil may be positioned perpendicular to or parallel to an imaginary line defining a synaptic region of the brain of a patient. In accordance with an embodiment of the present invention, the high power cable is capable of transferring between 400 joules and 1000 joules of energy and the charging switches 111 and discharge switches 112 comprise solid state thyristors.

During operation of the MS subsystem 110, the discharge switches 112 are commanded open (i.e., are electrically disconnected from the output of the storage capacitor bank 113) by the controller 116. The charging switches 111 are then commanded closed (i.e., are electrically connected to the input of the storage capacitor bank 113) by the controller 116. When the charging switches 111 close, the energy source 114 charges up the storage capacitor bank 113. In accordance with an embodiment of the present invention, the energy source 114 produces currents of between 5,000 amperes and 25,000 amperes and the storage capacitor bank 113 charges up to between 200 volts and 6000 volts.

After the storage capacitor bank 113 is charged, the controller 116 commands the charging switches 111 to open (i.e., electrically disconnect from the input of the storage capacitor bank 113) and commands the discharge switches 112 to close (i.e., electrically connect to the output of the storage capacitor bank 113). When the discharge switches 112 close, the electrical energy stored in the storage capacitor bank 113 discharges into the magnetic coil 115 as a flow of current.

The characteristics of the discharge is controlled by the controller 116 such that the parameters of the electric current sent through the magnetic coil 115 are predetermined. These electric current discharge parameters include pulse width, pulse magnitude, waveform shape, and frequency. In accordance with an embodiment of the present invention, the pulse width of the electric current discharge ranges between 10 microseconds and 2 milliseconds and peak currents delivered to the magnetic coil 115 range between 1 kiloampere and 100 kiloamperes.

The electric current discharge into the magnetic coil 115 generates a magnetic field having many of the same characteristics as the discharged electric current (e.g., pulse width, waveform shape, and frequency). For example, the magnitude of the resultant magnetic field is proportional to the magnitude of the electric current discharge. In accordance with an embodiment of the present invention, an intensity or magnitude of the resultant magnetic field ranges between 0.2 Tesla and 25 Tesla. The characteristics of the electric current discharge and the design and configuration of the magnetic coil 115 result in a focusing of the magnetic field in a certain spatial direction.

In accordance with an embodiment of the present invention, the magnetic coil 115 comprises wound and insulated metallic wire, such as copper, and is contained in a molded plastic housing. An inside diameter of the coil 115 ranges between 10 millimeters and 60 millimeters. An outside diameter of the coil 115 ranges between 40 millimeters and 100 millimeters. A number of turns of the coil 115 ranges between 20 turns and 80 turns.

The molded plastic housing also preferably contains a temperature sensor connected to an electronic circuit in order to monitor the temperature of the magnetic coil 115 within the housing during operation. The electronic circuit interfaces to the controller 116 in order to report the monitored temperature.

In accordance with another embodiment of the present invention, a ferromagnetic material is placed around the magnetic coil 115 to increase the effectiveness of the pulsed magnetic field. Also, a transformer may optionally be connected between the discharge switches 112 and the magnetic coil 115 to increase the magnitude of the pulsed current waveform through the coil 115.

When the magnetic coil is placed in close proximity to selected synaptic regions of the brain of the patient, the pre-polarized states of the selected synaptic regions may affect the focusing of the magnetic field within the brain. In one embodiment, the magnetic coil is implanted in the body of the patient. In another embodiment, the magnetic coil is not implanted, i.e., is external to the body of the patient. The pre-polarized states of the selected synaptic regions may be due to the naturally polarized states of these regions (i.e., induced electric charges that occur naturally within the brain), or they may be due to administering ENS therapy to affect the polarizations of the selected synaptic regions before administering MS therapy. Also, in accordance with various embodiments of the present invention, focusing of the magnetic field generated by the magnetic coil 115 within the brain of a patient may be enhanced by placing magnetic or paramagnetic material within synaptic regions of the brain. This may be accomplished via, for example, injection of magnetic or paramagnetic material into blood vessels or by using an external magnetic device and visual monitoring techniques as part of a surgical procedure.

Figures 6A, 6B, 6C:
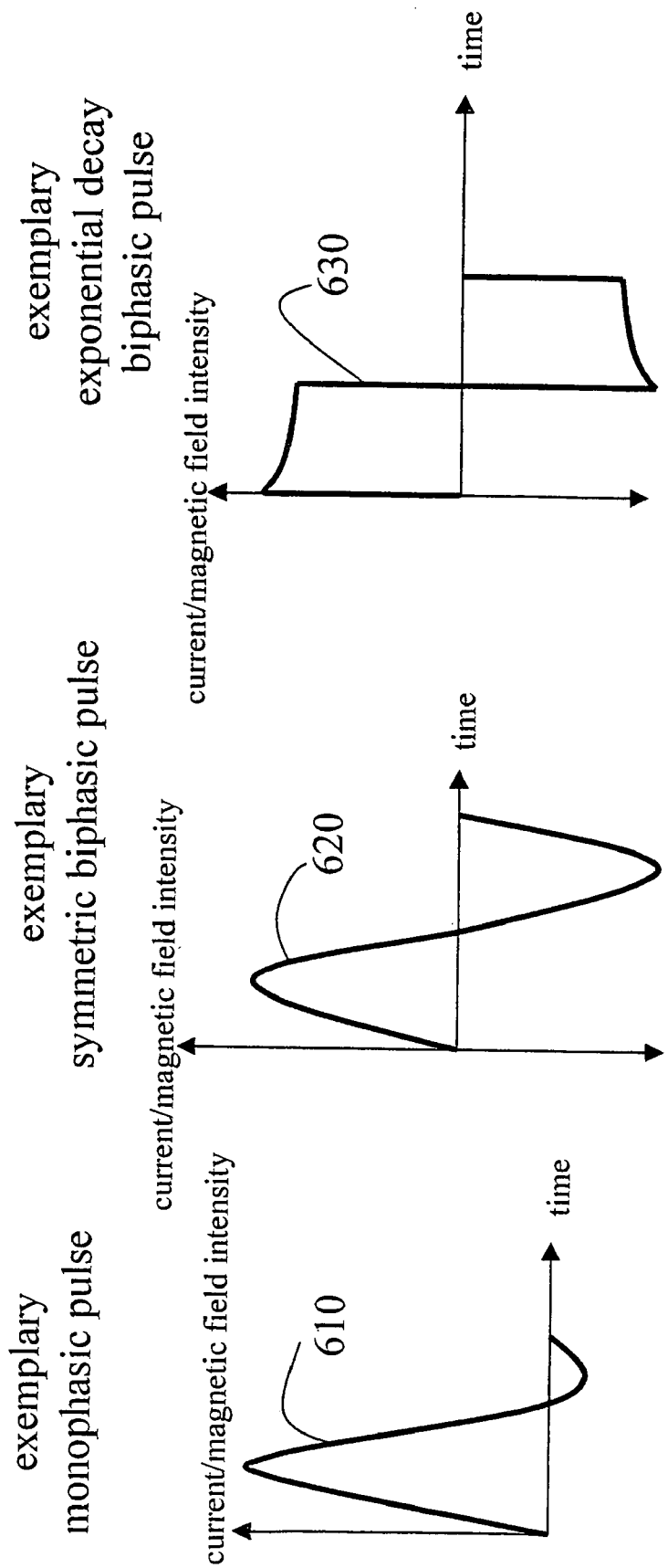
FIGS. 6A-6C are schematic illustrations of exemplary magnetic pulse shapes produced by the magnetic stimulation (MS) subsystem of FIG. 5, in accordance with an embodiment of the present invention.

FIGS. 6A-6C are schematic illustrations of exemplary magnetic pulse shapes produced by the magnetic stimulation (MS) subsystem 110 of FIG. 5, in accordance with various embodiments of the present invention. FIG. 6A illustrates an exemplary monophasic pulse shape 610 where most of the discharged current and magnetic field strength is in one direction. FIG. 6B illustrates an exemplary symmetric biphasic pulse shape 620 where the discharged current and resultant magnetic field strength is first directed in one direction, and then equally directed in an opposite direction. Such a biphasic pulse shape may be created by first charging the storage capacitor bank 113 in a positive direction with the energy source 114, discharging, and then charging the storage capacitor bank 113 in a negative direction, and then discharging again. FIG. 6C illustrates an exemplary exponential decay biphasic pulse shape 630. Such a pulse shape 630 may be generated by controlling a discharging time constant of the storage capacitor bank 113 into the magnetic coil 115 along with controlling the reversal of charging of the storage capacitor bank 113 in an opposite direction.

In accordance with an embodiment of the present invention, the controller 116 also interfaces to the storage capacitor bank 113 and the circuitry within the magnetic coil housing. As a result, the controller 116 regulates the capacitance of the storage capacitor bank 113, the conductance of the magnetic coil 115, and a resistance of the magnetic coil 115 in order to control a rise time and a decay time of each current pulse generated. The rise time ranges between 5 microseconds and 2000 microseconds, in accordance with an embodiment of the present invention.

Figure 7:
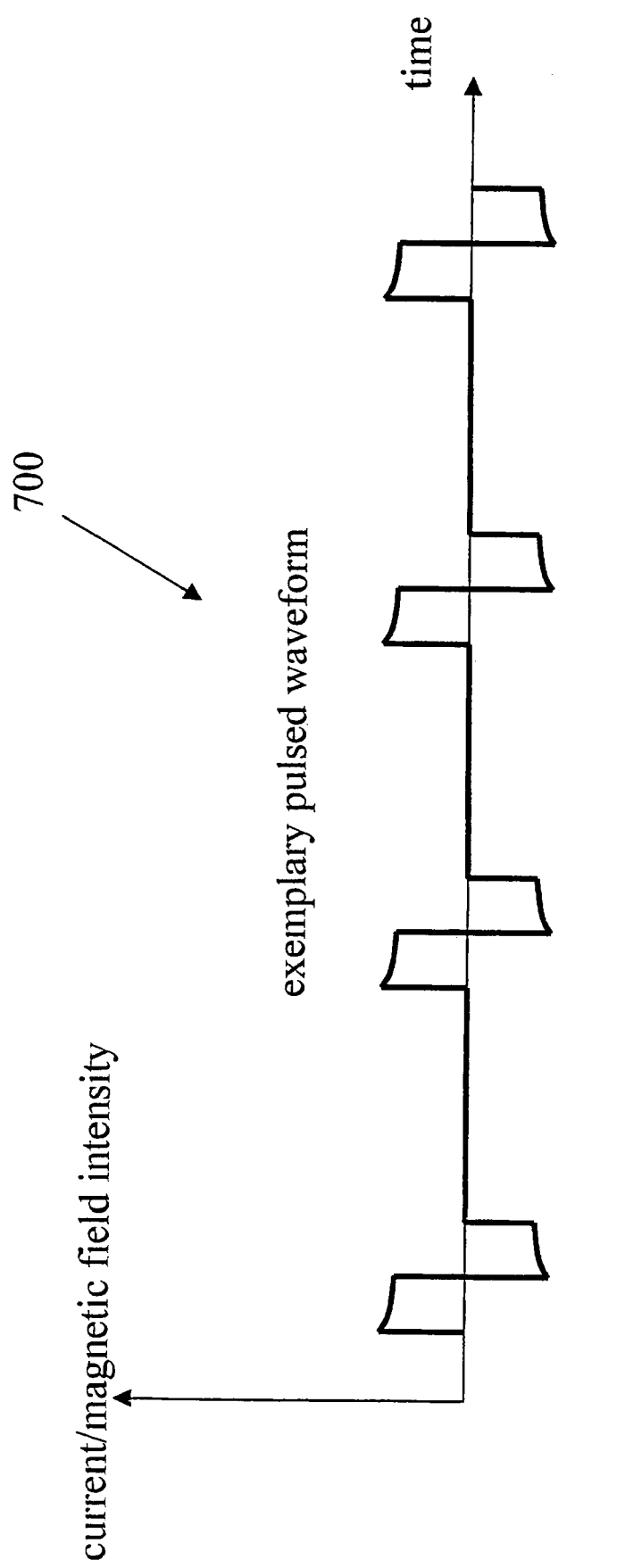
FIG. 7 is a schematic illustration of an exemplary pulsed waveform produced by the magnetic stimulation (MS) subsystem of FIG. 5 using the magnetic pulse shape of FIG. 6C, in accordance with an embodiment of the present invention.

The process of charging and discharging the storage capacitor bank 113 as described above may be repeated to generate a pulsed waveform comprising a train of magnetic field pulses. FIG. 7 is a schematic illustration of an exemplary pulsed waveform 700 produced by the magnetic stimulation (MS) subsystem 110 of FIG. 5 using the magnetic pulse shape 630 of FIG. 6C, in accordance with an embodiment of the present invention. The duration of a pulse train may range from between 0.1 seconds to 3600 seconds, more preferably from 1 second to 360 seconds.

An example of a clinical approach using the present invention involves treatment of epilepsy. VNS has been used therapeutically in treating epilepsy by initiation of an inhibitory polarization or hyper-polarization of neurons or nuclei in the brain to decrease or stop seizures. The effect of VNS can be augmented with MS which can produce a direct hyper-polarization or polarization of neurons or nuclei by focusing a magnetic field to modulate neuro-potential changes.

The waveform of a VNS signal may take various shapes such as a rectangular pulse or pulse train, a triangular pulse or pulse train, a logarithmic pulse or pulse train, and an exponential pulse or pulse train. The waveform of the MS signal can also be varied depending on the design of the magnetic coil 115, storage capacitor bank 113, etc. However, the major effort in MS strategy is directionality or focusing of the magnetic field waveform whether it is a pulsed waveform or otherwise.

In a patient with multiple pathologies, it is possible to alternate different stimulation parameters, each particular set of stimulation parameters being considered as most effective for a particular pathology. Each of the different stimulation parameters elicit a particular set of nerve action potentials, frequency of action potentials, etc.

ENS, such as VNS, can be used to prepare synaptic electrodynamics by changing polarization levels in critical synapses. This causes a focus enhancement for the action of MS and thus can increase the effectiveness of MS. Conversely, MS can initially act upon critical synapses to increase the effectiveness of ENS. Also, MS can be used to suppress activity in brain areas that may suppress the effect of ENS. Therefore, MS and ENS can mutually augment the therapeutic effect of the other therapy to increase overall therapeutic effectiveness.

Since ENS therapy such as VNS typically requires surgical implantation, it can be administered continuously to a patient and can be programmed over a wide range of time intervals. MS, however, is typically programmed or operated external to the patient such that its action is determined by the access of the patient to the MS subsystem or operator availability.

The relative use of MS and ENS depends on the specific illness, condition of the patient, etc. For example, in some cases it may be better to initiate ENS until a certain clinical outcome is achieved, and then initiate MS for optimum effectiveness, or do the reverse. Sometimes, it may be important for MS and ENS to be initiated simultaneously to produce a rapid clinical outcome. Such decisions are made based on the clinical diagnosis of each individual patient.

It is possible to select patients for MS/ENS therapy by using this treatment for relatively brief periods of time during monitoring (e.g., with MRI, etc.). In selection of patients for, for example, epilepsy, it may not be possible to stimulate from the surface of the skin with electrodes. However, it may be possible to focus a magnetic field on the appropriate nerves using MS techniques. As a result, the MS subsystem alone may be used to select patients for the implantable ENS subsystem in some circumstances.

Using MS in conjunction with ENS may not only increase effectiveness, but in addition, may reduce the time taken to reach effectiveness. For example, in epilepsy and depression, it has been demonstrated that, with VNS alone, it may take many months in some patients to achieve a maximum effectiveness possible. If a patient is observed to be slowly responding to VNS, then a program of MS in conjunction with VNS can be used to accelerate therapeutic effectiveness.

In depression, MS can be provided in a similar manner to electro-shock therapy (ECT), which produces a rapid effectiveness. However, MS offers the potential advantage of a much more benign side effect profile. Therefore, in one embodiment, treatment using the MS subsystem 110 alone may be provided to produce a rapid effect, which may then be prolonged by ENS therapy. During the scheduled treatment using MS therapy, this pattern can be repeated resulting in an overall increase in therapeutic effectiveness of ENS. The balance between ENS therapy and MS therapy is adjusted depending on the patient and the nature of the illness.

In accordance with another embodiment of the present invention, a collar coil is placed around the neck of the patient to stimulate the vagus nerve during MNS. The number of individual neurons activated in this manner is dependent on the power output of the MNS system. In accordance with an embodiment of the present invention, a chest coil is used to stimulate vagal nerves, sympathetic nerves, the heart, or any component of the heart such as, for example, the SA node.

An effectiveness of the MS subsystem may be tested by placing the magnetic coil 115 of the MS subsystem 110 on the skin of a patient over the ulnar, perenial, or sciatic nerves to observe a muscle twitch.

In accordance with various embodiments of the present invention, psychiatric, neurological, and other illnesses that may be treated with a combination of ENS and MS therapies include but are not limited to:

cancer, infections (e.g., viral, bacterial, fungal, etc.), poisoning (by, for example, drugs or chemicals), malnutrition, obesity, metabolic disorders (e.g., water and electrolyte metabolism disorders), endocrine disorders (e.g., disorders of the pituitary gland, thyroid gland, adrenal system, or reproductive system including pancreatic disorders such as diabetes and hypoglycemia), hypertension, renal disease and chronic renal failure, heart disease (e.g., arterial, muscular), skin diseases, autoimmune disorders, rheumatic disorders, blood disorders/diseases (e.g., leukemia), malabsorption disorders, Crohn's disease, ulcerative colitis, functional bowel disorders, irritable bowel syndrome, colonic diverticular disease, liver disorders (e.g., hepatitis, cirrhosis, transplantation side effects), heart failure, pulmonary circulation disorders, respiratory failure, raised intracranial pressure, chest diseases, respiratory disease, allergic rhinitis, asthma, lung disease (e.g., pneumonia), neoplastic disorders (e.g., pulmonary metastases, pleural tumors), diseases of the skeleton (e.g., rheumatoid arthritis, osteoporosis), glomerular diseases, sexually transmitted diseases (e.g., HIV/AIDS, herpes), eye and ear disorders (e.g., eye movement disorders, balance disorders), headaches (e.g., migraine headaches, neuromuscular headaches), sleeping disorders including narcolepsy and chronic insomnia, seizures, epilepsy, eating disorders including anorexia nervosa, bulimia, and compulsive overeating, neuro-psychiatric disorders including depression, schizophrenia, bi-polar disorder, borderline personality disorder, anxiety, dementia including cortical, sub-cortical, multi-infarct, Alzheimer's disease, Pick's disease, Parkinson's disease, cerebral palsy, spasticity, involuntary movement and chronic nervous illnesses, multiple sclerosis, muscle disorders (e.g., muscular dystrophy), drug-related disorders (e.g., alcoholism), inherited disorders.

The problem of cancer is related directly to the subject of cell regulation and differentiation. A normal differentiated cell that was once performing certain functions in cooperation with its neighbors can somehow undergo a fundamental change that converts it to a malignant state. It is released from various restraints that hold cell division in check. When it is transformed to a cancerous state, a cell that was non-cycling re-enters the cell cycle and proliferates wildly to produce billions of altered cells, which constitute the tumor or cancer.

Uncontrolled growth is just one feature a cell acquires when it is transformed to the malignant state. The cancer cell also gains the property of immortality in the sense that it can multiply indefinitely in cell culture, unlike normal cells that lose the ability to divide after about fifty cell generations and then die. Cancer cells also become less responsive to feedback mechanisms that control the growth of normal cells, both in culture and in vivo. For example, normal cells divide and form a neat, single-cell layer when grown on a culture dish. Cell division shuts down when the entire surface of the dish is covered. Malignant cells, on the other hand, are not confined to the orderly single layer, but grow on top of one another in disordered piles.

Cell division has not shut down in response to the presence of other cells. The malignant cell has lost the property of contact inhibition. Experiments suggest that it is not the actual contact among normal cells that is the basis for shutting down cell division, but rather the degree to which cells spread out. A cell that is able to spread out on a surface has a shorter growth cycle. The rate of protein synthesis decreases in the more rounded-up cell, even in the absence of contact with other cells. Apparently, when a normal cell contacts other cells, it cannot spread out to its fullest extent. This reduces the rate at which it makes proteins, one or more of which may be needed for cell division. Cancer cells, even when they cannot flatten out on a culture dish, still appear unaffected and continue to proliferate.

This may be related to the membrane potential whose value has been changed from that required for normal growth. The membrane potential is partially dependent on the protein (membrane) configuration and charge. It is reasonable to conclude that, if the membrane potential is restored by an electrical field, normal growth and cycling would ensue. The contact inhibition might also be due not only to a mechanical contact inhibition, but a repulsion due to like charges due to the membrane potential acting between cells by electrical induction.

Such a list of changes accompanying the malignant transformation indicates that the cellular control mechanism has been altered profoundly in the transition from the normal to the cancerous state. There is reason to suspect that the membrane potential is an important component of the control mechanism, and a return of the membrane potential to its normal state will tend to reverse the malignant process, and stop malignant growth and the cancerous process.

Certain cells are programmed, or regulated, to die as differentiation of body parts proceed. There may be a limit to the number of cell doublings that is thereby programmed or regulated. For instance, in contrast to normal cells, many tumor cells can be grown indefinitely in culture. They would appear to have escaped senescence and are termed "immortal".

The activation of different neurons by ENS is directed to modulate the growth control centers in the brain (releasing growth hormone, etc.) to thereby prevent cancerous growth and/or a hospital based unit may be used to produce a large magnetic field (1-10 Tesla). Such treatments can be much more frequent than radiation or chemotherapy (less side effects, etc.). Evidence for the effectiveness of such treatments has been obtained in the laboratory on animals (rats). This includes new observations on the behavior of cancerous cells and also data on the charged membrane characteristics of these cells.

There is another advantage in that these treatments do not interfere with the action of the major cancer therapies (chemotherapy, radiation, and surgery). Thus, it can be used in conjunction with these treatments. The major advantage in relation to these other cancer therapies are safety (non-toxicity) and a different mechanism of action. The side effects of the major cancer treatments at present cause strict limitations on the use and scope of these treatments.

The American Cancer Society data of 1986 indicate that, in the United States, the incidence (new cases) of cancer was 956,000 and that 478,000 Americans died from cancer. There is a worldwide incidence of new cancer cases of over 7.2 million and 4.9 million cancer deaths and the worldwide prevalence of cancer is estimated to be about 15.1 million. It is approximated that one out of three persons in the United States will contract cancer. In addition to a large hospital based unit, a small portable unit will be used in the physician's office or perhaps in the patient's home.

An example of one mechanism of action of ENS or MS is the following. Unstable replication of cells may be initiated by instability in the hypothalamus (and hypophysis) consisting of growth hormone and corticotrophic hormones (causing release of corticosteroids). Instability of hypothalamic regulation of these hormones may cause abnormal cell replication without cell differentiation. Since these cells do not differentiate, they continue to replicate primitive cells. Stabilization of hypothalamic regulation results in hormonal stabilization and satisfactory differentiation.

The application or treatment for H.I.V. (AIDS), or other viral infections, can be accomplished in a similar manner to cancer, since the mechanism of action is on the membrane potential, where the membrane potential is stabilized to control viral growth or to prevent penetration of viral particles into the cell.

In summary, the present invention provides systems and methods for providing both ENS and MS therapies to a patient. ENS therapy allows a high level of control of the therapeutic agent (i.e., an electrical pulse under microcomputer regulation), which is applied directly to specific nerves. MS, on the other hand, provides a great degree of flexibility since it can be provided non-invasively and the therapeutic stimulus is not limited to one specific structure. Systems of the present invention combine ENS and MS to provide an optimum combination of precision and flexibility which other therapies lack.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but will include all embodiments falling within the scope of the appended claims.

What is claimed is:

1. A therapeutic method for treating a medical condition in a patient, said method comprising:
   diagnosing a medical condition of a patient;
   administering an electric nerve stimulation (ENS) therapy to a first body location of said patient; and
   administering a magnetic stimulation (MS) therapy to a second body location of said patient to enhance effectiveness of said therapy,
   wherein said administering of said magnetic stimulation therapy is independent of any unwanted neural activity induced by said electric nerve stimulation therapy,
   and wherein said administering of said electric nerve stimulation therapy is independent of any unwanted neural activity induced by said magnetic stimulation therapy.

2. The method of claim 1 wherein said electrical nerve stimulation (ENS) therapy comprises vagus nerve stimulation (VNS).

3. The method of claim 1 wherein said electrical nerve stimulation (ENS) therapy comprises cranial nerve stimulation (CNS).

4. The method of claim 1 wherein said MS therapy comprises transcranial magnetic stimulation (TMS).

5. The method of claim 1 wherein said medical condition is a neuropsychiatric disorder.

6. The method of claim 1 wherein said magnetic stimulation (MS) therapy is administered until a desired clinical outcome is achieved, followed by said administering of said electric nerve stimulation (ENS) therapy for enhanced effectiveness.

7. The method of claim 1 wherein said first body location comprises a first set of nerves in the brain and said second body location comprises a second set of nerves in the brain.

8. The method of claim 1 wherein said electric nerve stimulation (ENS) therapy and said magnetic stimulation (MS) therapy are both administered to a same set of nerves of a brain.

9. The method of claim 1 wherein said electric nerve stimulation (ENS) therapy changes a polarization of synaptic membranes in a nuclei or center of the brain of the patient.

10. The method of claim 1 wherein said magnetic stimulation (MS) therapy changes a polarization of synaptic membranes in a nuclei or center of the brain of the patient.

11. The method of claim 1 wherein said MS therapy is applied to tissue remote from the brain of the patient.

12. The method of claim 1 wherein said magnetic stimulation (MS) therapy is administered to said patient after said electric nerve stimulation (ENS) therapy is administered to said patient.

13. The method of claim 1 wherein said magnetic stimulation (MS) therapy is administered to said patient before said electric nerve stimulation (ENS) technique is administered to said patient.

14. The method of claim 1 further comprising temporally alternating said administration of said electric nerve stimulation (ENS) therapy and said administration of said magnetic stimulation (MS) therapy a plurality of times.

15. The method of claim 1 wherein said electric nerve stimulation (ENS) therapy and said magnetic stimulation (MS) therapy are administered simultaneously.

16. The method of claim 1 wherein said magnetic stimulation (MS) therapy is administered to nuclear synaptic areas including cell bodies, dendrites, and pre-synaptic terminals where a membrane potential exists and an action potential does not exist.

17. The method of claim 1 wherein said electric nerve stimulation (ENS) therapy is administered until a desired clinical outcome is achieved, followed by said administering of said magnetic stimulation (MS) therapy for enhanced effectiveness.

18. The method of claim 1 wherein said step of administering a MS therapy comprises:
   applying a magnetic field to a pre-selected synaptic region of the brain of the patient;
   monitoring a physiological response associated with said application of said magnetic field; and
   selectively adapting at least one parameter of said magnetic field in response to said monitored physiological response.

19. The method of claim 18 wherein said magnetic field comprises a pulsed magnetic field.

20. The method of claim 18 wherein said magnetic field comprises an alternating magnetic field.

21. The method of claim 18 wherein said magnetic field comprises a steady magnetic field.

22. The method of claim 18 wherein said physiological response includes changes in electroencephalogram (EEG) activity of said brain.

23. The method of claim 18 wherein said selectively adapting said at least one parameter of said magnetic field results in changing said physiological response such that said change in said physiological response indicates a reduction in said symptoms.

24. The method of claim 18 wherein said at least one parameter of said magnetic field comprises a pulse width, a pulse repetition frequency, a magnetic intensity, and an orientation.

25. The method of claim 18 wherein said step of applying a magnetic field comprises:
   providing a magnetic generator to generate said magnetic field upon activation of said magnetic generator;
   setting at least one parameter of said magnetic generator, based on said symptoms; and
   stereotaxically positioning a magnetic coil of said magnetic generator in relation to said brain such that said magnetic field becomes focused on a selected synaptic region of said brain to polarize said selected synaptic region in a predetermined manner upon activation of said magnetic generator.

26. The method of claim 18 wherein said step of monitoring said physiological response comprises contacting at least one electrode on the scalp of said patient to monitor electroencephalogram (EEG) changes of said brain.

* * * * *